(12) United States Patent
Dannecker et al.

(10) Patent No.: US 6,264,932 B1
(45) Date of Patent: *Jul. 24, 2001

(54) AGENT AND METHOD FOR PERMANENT SHAPING OF HAIR AND METHOD FOR THE PRODUCTION OF N-ALKYLMERCAPTOACETAMIDES

(75) Inventors: Beate Dannecker, Darmstadt; Günther Lang, Reinheim; Wolfgang Hanefeld; Heiko Walther, both of Marburg/Lahn, all of (DE)

(73) Assignee: Wella Aktiengesellschaft, Darmstadt (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/269,471
(22) PCT Filed: Jul. 14, 1998
(86) PCT No.: PCT/EP98/04361
§ 371 Date: Mar. 27, 1999
§ 102(e) Date: Mar. 27, 1999
(87) PCT Pub. No.: WO99/06013
PCT Pub. Date: Feb. 11, 1999

(30) Foreign Application Priority Data

Jul. 31, 1997 (DE) .............................................. 297 13 619

(51) Int. Cl.⁷ ...................................................... A61K 7/09
(52) U.S. Cl. ........................ 424/70.2; 424/70.1; 132/203
(58) Field of Search ................................... 132/210, 203; 424/72, 70.1, 70.2

(56) References Cited

U.S. PATENT DOCUMENTS 2,106,697 * 1/1938 Munro et al. ........................ 260/124
5,061,483 * 10/1991 Tieckelmann et al. ................. 424/72
5,085,860 * 2/1992 Junino et al. ........................... 424/72

FOREIGN PATENT DOCUMENTS

| 948186 | 8/1956 | (DE) . |
| 972 424 | 7/1959 | (DE) . |
| 1 144 440 | 2/1963 | (DE) . |

* cited by examiner

Primary Examiner—Thurman K. Page
Assistant Examiner—Liliana Di Nola-Baron
(74) Attorney, Agent, or Firm—Michael J. Striker

(57) ABSTRACT

The aqueous ready-to-apply composition for permanent waving of hair has a pH of 4 to 8.5 and from 3 to 28% by weight of at least one N-alkylmercaptoacetamide of formula (I):

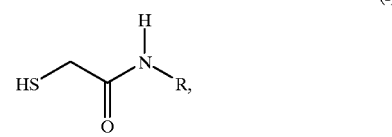

wherein R represents a straight-chain alkyl group having from 3 to 6 carbon atoms or a straight-chain hydroxyalkyl group having from 3 to 6 carbon atoms; or a salt thereof; and at least one standard cosmetic additive ingredient, such as thickeners, wetting agents and emulsifiers, perfume oils, conditioners and buffer substances. The ready-to-apply composition can be made by mixing two or more components, one of which contains the N-alkylmercaptoacetamide. A method for permanent waving of hair using the ready-to-apply composition is also described. A process for making the N-alkylmercapto-acetamides includes reacting a suitable amine with methylthioglycolate under a protective gas atmosphere at temperatures that are not greater than 30° C.

8 Claims, No Drawings

AGENT AND METHOD FOR PERMANENT SHAPING OF HAIR AND METHOD FOR THE PRODUCTION OF N-ALKYLMERCAPTOACETAMIDES

BACKGROUND OF THE INVENTION

1. Field of the Invention

The present invention relates to a composition for permanent hair waving based on straight-chain N—$C_3$—to N—$C_3$–$C_6$-alkyl- or N—$C_3$–$C_6$-hydroxyalkyl-substituted mercaptoacetamides, as the keratin-reducing ingredient, and to a method for permanent hair waving using this composition.

2. Prior Art

The classic technique for permanent hair waving is familiarly based on two treatment steps: In the first step, the cystine-disulfide bridges of the keratin of the hair are opened by the action of an agent that contains a reducing ingredient (waving composition). The hair is then put into the desired form. In a second step, cystine-disulfide bonds are closed again using a fixative, that is, an agent containing an oxidant ingredient.

As the pioneering work in German patents 948 186 and 972 424 demonstrate, thioglycolic acid, for instance in the form of an ammonium or monoethanolamine salt, is used as a classic permanent hair waving reducing agent. Other typical reducing agents are 2-mercaptopropionic acid (thiolactic acid), 3-mercaptopropionic acid, cysteine, and derivatives of these compounds, as well as certain mercaptocarboxylic acid esters.

Alkaline-adjusted preparations based on mercaptocarboxylic acid esters, despite being adequately effective, cause hair damage, which is expressed for instance in increased hair breakage. Often, these compositions also undesirably stress the scalp. Finally, the unpleasant odor of the reducing agents used requires intensive perfuming of the products. By using 2-mercaptopropionic acid, it is possible to solve some of these problems. However, in comparison to thioglycolic acid, which is widely used, thiolactic acid produces weaker waves.

For gentle, permanent waving of damaged and especially bleached or dyed hair, waving compositions that are adjusted to be slightly acidic to neutral are preferably used. From a professional standpoint, over the last 35 years, the thioglycolic acid esters have proved to be the reducing agents best suited for this purpose.

A major disadvantage of acidic hair waving compositions based on thioglycolic acid esters, however, is that they are poorly tolerated by the eyes and skin, and the sensitizing effect of the thioglycolic acid esters, so that the use of these hair waving compositions is widely avoided at present. Instead of the mercaptocarboxylic acid esters, mercaptoacetamides such as thioglycolic acid amide or alkyl- or hydroxyalkyl-substituted amides have also been used. Such compounds are known from German Patent DE-C1 144 440 and European Patent EP-A 0 455 457. Like the mercaptocarboxylic acid esters, these substances have a high waving potential at low pH values, but in terms of toxicology they are even more critical than the mercaptocarboxylic acid esters.

SUMMARY OF THE INVENTION

It is therefore the object of the invention to make available a composition and a method for permanent hair waving that both in the acidic and the slightly alkaline range (pH—2 to 9.5), and above all in the pH range from 4.0 to 8.5, makes gentle, uniform hair waving possible, has no or only a slight sensitizing potential, and furthermore has a stronger hair waving potential than 2-mercaptopropionic acid (thiolactic acid).

Surprisingly, it has now been discovered that the above disadvantages can be overcome by the use of certain N-alkylmercaptoacetamides, and that they have a stronger hair waving potential than thiolactic acid.

The subject of the present invention is therefore a composition for permanent hair waving, which is characterized in that as its keratin-reducing ingredient, it contains an N-alkylmercaptoacetamide of the formula

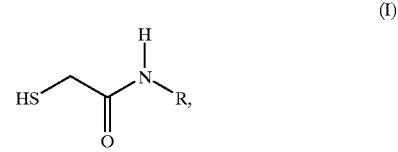

(I)

in which R stands for a straight-chain alkyl radical with from 3 to 6 carbon atoms, or a straight-chain hydroxyalkyl radical with from 3 to 6 carbon atoms, or its salt.

DESCRIPTION OF THE PREFERRED EMBODIMENTS

Preferably, the straight-chain hydroxyalkyl radical has one or two hydroxyl groups.

Preferred N-alkylmercaptoacetamides of formula (I) are N-propyl-2-mercaptoacetamide, N-(2'-hydroxypropyl)-2-mercaptoacetamide, and N-(3'-hydroxypropyl)-2-mercaptoacetamide.

Possible salts include above all the hydrogen salts of the acids in the group comprising hydrochloric acid, sulfuric acid, acetic acid or citric acid.

The N-alkylmercaptoacetamide of formula (I) is preferably contained as the sole keratin-reducing ingredient in the composition. However, it may also be used in combination with other keratin-reducing ingredients—such as thioglycolic acid, thiolactic acid, 2-hydroxy-3-mercaptopropionic acid, cysteamine and cysteamine derivatives such as alkyl- or acylcystamine or cysteine and cysteine derivatives, such as cysteine-(2-hydroxyethyl)ester or L-cysteine glycerine ester or sulfites.

The N-alkylmercaptoacetamide of formula (I) is contained in the ready-to-use composition for permanent hair waving in a quantity of from 3 to 28 weight-%, preferably 5 to 21 weight-%.

The ready-to-use hair waving composition preferably has a pH value of from 2.0 to 9.5 and especially preferably from 4.0 to 8.5. As an alkalizing agent or agent for adjusting the pH value, ammonia or caustic soda is especially suitable, but water-soluble, physiologically tolerable salts of organic and inorganic bases can also be considered, such as ammonium hydrogen carbonate. To establish an acidic pH value, hydrochloric acid, acetic acid or citric acid can be used in particular.

The waving composition may be sold in single- or dual- or triple-component packages; the composition may be in the form of an aqueous solution, or an emulsion, or in thickened water-based form, especially a creme, gel, foam or paste.

It is understood that the waving composition may contain all the usual and known additives for such compositions, such as thickeners, such as bentonite, fatty acids, starch, polyacrylic acid and its derivatives, cellulose derivatives, alginates, vaseline, and paraffin oils; wetting agents or emulsifiers from the classes of anionic, cationic, amphoteric or nonionic surfactants, such as fatty alcohol sulfates, fatty alcohol ether sulfates, alkyl sulfonates, alkylbenzene sulfates, quaternary ammonium salts, alkyl betaines, ethoxylated alkylphenols, fatty acid alkanolamides or ethoxylated fatty acid esters; and opacifiers, such as polyethyleneglycol esters; alcohols, such as ethanol, propanol, isopropanol, polyols such as 1,2- or 1,2-propanediol, 1,2-, 1,3- or 1,4-butanediol, 1,2-pentanediol and glycerine; sugars such as D-glucose; solubilizers, stabilizers, buffer substances, perfume oils, dyes, and hair-conditioning and hair-care ingredients, such as cationic polymers, lanolin derivatives, cholesterol, pantothenic acid, and betaine.

The aforementioned ingredients are used in quantities usual for such purposes; for example, the wetting agents and emulsifiers in concentrations of a total of 0.2 to 30 weight-%, the alcohols in a total quantity of 0.1 to 20 weight-%, the opacifiers, perfume oils and dyes in a quantity of 0.01 to 1 weight-% each, the buffer substances in a total quantity of 0.1 to 10 weight-%, and sugars, solubilizers, stabilizers and hair-conditioning and hair-care ingredients in a quantity of 0.1 to 5 weight-% each, while the thickeners and solubilizers may be contained in this composition in a total quantity of 0.5 to 20 weight-%.

So-called swelling agents and penetrating substances can also be added to this composition, examples being dipropyleneglycol monomethyl ether, 2-pyrrolidone or imidazolidin-2-one, in a quantity of 1 to 30 weight-%, and to avoid making the hair too kinky, dithio compounds, such as dithioglycolic acid, dithiolactic acid, the disulfides of these compounds, or their salts.

By varying the pH value, a composition can be made available that is universally suitable for every hair structure, optionally with the additional application of heat. The composition brings about an elastic, durable and uniform waving from the root of the hair to the ends, without eliciting allergic or sensitizing reactions.

The present invention also relates to a method for permanent hair waving, in which before and/or after the hair is set in the desired way, the hair is treated with a waving composition, rinsed with water, then oxidatively treated, rinsed with water, optionally set for water waving and then dried, which is characterized in that as the waving composition, the compositions of the invention as described above are used.

In a preferred embodiment of the method of the invention, the hair is first washed with a shampoo and then rinsed with water. Next, the towel-dried hair is divided into individual strands and wound onto curlers with a diameter of 5 to 30 millimeters, preferably 5 to 15 millimeters. The hair is then treated with an adequate quantity for hair waving, preferably 60 to 120 grams, of the described waving composition of the invention.

After an action time sufficient for the permanent waving of the hair, which depending on the nature of the hair, on the pH value and the waving effectiveness of the waving composition, and on the temperature employed amounts to from 5 to 30 minutes (10 to 30 minutes if heat is not applied; 5 to 20 minutes with the application of heat), the hair is rinsed with water and then oxidatively post-treated ("fixed"). The post-treatment composition is used in a quantity of preferably 80 to 100 grams, depending on the fullness of the hair.

For the oxidative post-treatment, with the hair either wound up on curlers or not, any arbitrary post-treatment composition suitable for such a treatment can be used. Examples of oxidants that can be used in such post-treatment compositions are potassium bromate, sodium bromate, sodium perborate, urea peroxide and hydrogen peroxide. The concentration of the oxidant varies, depending on the application time (as a rule, 5 to 15 minutes) and the application temperature. Normally, the oxidant is present in the ready-to use aqueous post-treatment composition in a concentration of 0.5 to 10 weight-%. The composition for oxidative post-treatment can naturally also include other substances, such as wetting agents, hair-care substances such as cation-active polymers, weak acids, buffer substances or peroxide stabilizers, and may be in the form of a aqueous solution, an emulsion, or a thickened water-based form, in particular a creme, gel or paste. These typical additives may be contained in the post-treatment composition in a quantity of 0.1 to 10 weight-%, in particular. Next, the curlers are removed. If necessary, the hair after being taken down from the curlers is oxidatively post-treated yet again. The hair is then rinsed with water, optionally set for a water wave, and finally dried.

Completely surprisingly, the preferred N-alkylmercaptoacetamides, which are N-propyl-2-mercaptoacetamide, N-(2'-hydroxypropyl)-2-mercaptoacetamide, and N-(3'-hydroxypropyl)-2-mercaptoacetamide, have substantially lower sensitization rates than their closest relatives in permanent waving ingredients, the N-alkylmercaptoacetamides known from the prior art as defined by German Patent DE-C1 144 440 and European Patent EP-A 0 455 457, that is, N-methylmercaptoacetamide and N-hydroxyethylmercaptoacetamide.

The production of the N-alkylmercaptoacetamide of formula (I) is done by reacting the corresponding amine at a temperature of not over 30° C. with methylthioglycolate in a protective gas atmosphere, extraction in a suitable solvent, and ensuing flash distillation.

The following examples are intended to explain the subject of the invention in further detail, but without limiting the subject to these examples.

PRODUCTION EXAMPLES

Example 1

Production of N-Propyl-2-mercaptoacetamide 118 g (2 mol) of n-propylamine are first put in a 500-ml three-neck flask. Slowly, 106.24 g of methylthioglycolate are added drop by drop, in such a way that the temperature does not exceed 30° C. The starting mixture is flushed with argon and stirred for 2 days at room temperature.

The mixture is acidified (pH 2–4) with 36% hydrochloric acid while being chilled with ice and is then extracted to exhaustion using ethyl acetate. The solvent is distilled off in a vacuum in the reflux evaporator; the residue is brought to a pH of 7.0 by adding caustic soda and then shaken out again with ethyl acetate. The combined fractions are dried over sodium sulfate and inspissated. The residue then is distilled into the pure product by flash distillation at a maximum of 0.01 Torr. The yield is 115 g (86%).

Analysis:
a) $^1$H-NMR (CDCl$_3$):

| δ (ppm) | | |
|---|---|---|
| 6.79 | (bulbous, —NH) |
| 3.20 | (t, 2H, + NH—CH$_2$) |
| 3.20 | (s, 2H, HS—CH$_2$—CO) |
| 1.85 | (bulbous, 1H, HS) |
| 1.52 | (m, 2H, NH—CH—CH$_2$) |
| 0.90 | (t, 2H, CH$_2$—CH$_3$) | b) $^{13}$C-NMR (CDCl$_3$):

| δ (ppm) | | |
|---|---|---|
| 169.18 | (—C=O) |
| 41.83 | (NH—CH) |
| 28.36 | (HS—CH$_2$) |
| 22.72 | (NH—CH—CH$_2$—CH$_3$) |
| 11.37 | (CH$_2$—CH$_3$) | c) MS (70 e V, EI, RT)
   m/z (%)=
   (M$^+$)=133 (47.68) 100 (29.1), 86 (24.58), 58 (8.6), 47 (25.67), 43 (100)
d) Thioltitration: 95.78%
e) Elemental analysis: C$_5$H$_{11}$NOS (MW: 133.21)
   Calculated: C 45.08, H 8.32, N 10.51, S 24.07
   Found: C 44.72, H 8.12, N 10.18, S 23.71
f) IR (NaCl slides)

| 3293s | (NH) |
|---|---|
| 3084-2876s | (CH$_2$) |
| 2552w | (SH) |
| 1652s | (N-monosubstituted amide) |
| 1559s | (N-monosubstituted amide) | g) HPLC: The results of the HPLC showed 98.07 area % for the compound.
   (Column: C 18 5U, 250 mm×4.6 mm; flow agent acetonitrile:buffer[4 g KH$_2$PO$_4$+0.8 g octanesulfonic acid sodium salt+2 ml H$_3$PO$_4$]=25: 75; flow rate 0.5 ml/min; wavelength 200 nm)
h) pKs: 8.451 (H$_2$O)
i) UV-max: 209.8 nm (acetonitrile:buffer=25:75)
i) Boiling point: 76° C. at 0.01 Torr Example 2

Production of N-(2'-Hydroxypropyl)-2-mercaptoacetamide 150.22 g (2 mol) of 1-amino-2-propanol are first put in a 500-ml three-neck flask. Slowly, 106.24 g (1 mol) of mercaptoacetic acid methyl ester are added drop by drop, in such a way that the temperature does not exceed 30° C. The starting mixture is flushed with argon and stirred for 2 days at room temperature.

The mixture is acidified (pH 2–4) with 36% hydrochloric acid while being chilled with ice and is then extracted to exhaustion using ethyl acetate. The solvent is distilled off in a vacuum in the reflux evaporator; the residue is brought to a pH of 7.0 by adding caustic soda and then shaken out again with ethyl acetate. The combined fractions are dried over sodium sulfate and inspissated. The applicable residue is distilled into the pure product by flash distillation at a maximum of 0.01 Torr. The yield is 95 g (64%).

Analysis:
a) $^1$H-NMR (CDCl$_3$):

| δ$_H$ (ppm) | | |
|---|---|---|
| 6.70 | (bulbous, —NH) |
| 3.93 | (m, 1H, CH) |
| 3.44 and 3.14 | (m, 1H each, NH—CH$_2$) |
| 3.26 | (s, 2H, HS—CH$_2$—CO) |
| 2.07 | (t, 1H, HS) |
| 1.21 | (d, 3H, CH$_3$) | b) $^{13}$C-NMR (CDCl$_3$):

| δ$_C$ (ppm) | | |
|---|---|---|
| 170.71 | (—C=0) |
| 67.00 | (NH—CH$_2$—CH) |
| 47.38 | (NH—CH$_2$) |
| 28.24 | (HS—CH$_2$) |
| 20.87 | (CH$_3$) | c) MS (70 e V, EI, RT)
   m/z (%)=
   (M$^+$)=149 (8.39) 131 (47.08), 105 (100), 84 (27.49), 72 (72.76), 58 (57.75), 56 (32.11), 47 (59.94)
d) Thioltitration: 97.88%
e) Elemental analysis: C$_6$H$_{13}$NOS (MW: 149.21)
   Calculated: C 40.25, H 7.43, N 9.39, S 21.49
   Found: C 40.11, H 7.42, N 9.12, S 21.53
f) IR (KBr)

| 3314s | (OH) |
|---|---|
| 3090-2927s | (CH$_2$) |
| 2549w | (SH) |
| 1657s | (N-monosubstituted amide) |
| 1554s | (N-monosubstituted amide) | g) HPLC: The results of the HPLC showed 98.88 area % for the compound.
   (Column: C 18 5U, 250 mm×4.6 mm; flow agent acetonitrile:buffer[4 g KH$_2$PO$_4$+0.8 g octanesulfonic acid sodium salt+2 ml H$_3$PO$_4$]=25:75; flow rate 0.5 ml/min; wavelength 200 nm)
h) pKs: 7.865 (H$_2$0)
i) UV-max: 218.0 nm (acetonitrile:buffer=25:75)
i) Boiling point: 108° C. at 0.01 Torr Example 3

Production of N-(3'Hydroxypropyl)-2-mercaptoacetamide 150.22 g (2 mol) of 3-amino-1-propanol are first put in a 500-ml three-neck flask. Slowly, 106.24 g (1 mol) of mercaptoacetic acid methyl ester are added drop by drop, in such a way that the temperature does not exceed 30° C. The starting mixture is flushed with argon and stirred for 2 days at room temperature.

The mixture is acidified (pH 2–4) with 36% hydrochloric acid while being chilled with ice and is then extracted to exhaustion using ethyl acetate. The solvent is distilled off in a vacuum in the reflux evaporator; the residue is brought to a pH of 7.0 by adding caustic soda and then shaken out again with ethyl acetate. The combined fractions are dried over sodium sulfate and inspissated. The applicable residue is distilled into the pure product by flash distillation at a maximum of 0.01 Torr. The yield is 63 g (42%).

Analysis:

a) $^1$H-NMR (CDCl$_3$):

| $\delta_H$ (ppm) | 7.062 | (bulbous, —NH) |
|---|---|---|
| | 3.64 | (m, 2H, CH$_2$—OH) |
| | 3.42 | (m, 2H, CH$_2$—CH$_2$—CH$_2$—OH) |
| | 3.22 | (d, 2H, HS—CH$_2$—CO) |
| | 2.04 | (t, 1H, CH$_2$—OH) |
| | 1.72 | (t, 1H, HS) |
| | 1.69 | (m, 2H, CH$_2$—CH$_2$—CH$_2$—OH) | b) $^{13}$C-NMR (CDCl$_3$):

| $\delta_C$ (ppm) | 170.59 | (—C=O) |
|---|---|---|
| | 59.86 | (NH—CH$_2$) |
| | 37.06 | (CH$_2$—OH) |
| | 31.99 | (CH$_2$—CH$_2$—CH$_2$—OH) |
| | 28.53 | (HS—CH$_2$) | c) MS (70 e V, EI, RT)

m/z (%)=

(M$^+$)=149 (36.13) 131 (36.58), 116 (31.62), 105 (23.15), 102 (100), 84 (72.8), 76 (24.49), 56 (66.29)

d) Thioltitration: 94.063% e) Elemental analysis: C$_5$H$_{11}$NOS (MW: 149.21)

Calculated: C 40.25, H 7.43, N 9.39, S 21.49

Found: C 40.21, H 6.99, N 9.05, S 21.53 f) IR (NaCl)

| 3299s | (NH) |
|---|---|
| 3086-2918s | (CH$_2$) |
| 2546w | (SH) |
| 1651s | (N-monosubstituted amide) |
| 1551s | (N-monosubstituted amide) | g) HPLC: The results of the HPLC showed 93.19 area % for the compound.

(Column:C 18 5U, 250 mm×4.6 mm; flow agent acetonitrile:buffer[4 g KH$_2$PO$_4$+0.8 g octanesulfonic acid sodium salt+2 ml H$_3$PO$_4$]=25:75; flow rate 0.5 ml/min; wavelength 200 nm)

h) pKs: 8.406 (H$_2$0)

i) UV-max: 223.2 nm (acetonitrile:buffer=25:75)

i) Boiling point: 115° C. at 0.01 Torr

Example 4

Comparison of Waving Effectiveness

The waving effectiveness of the compound was determined, using glycerine monothioglycolate as a comparison substance, using 10 waving solutions at a pH of 7, 8 and 9. Counted strands of previously bleached and thus damaged Central European hair (approximately 100 hairs per strand) 16.5 centimeters in length were wound up, wet, onto spiral curlers (inside diameter: 3 millimeters) and after conditioning in a climate-controlled room (temperature 20° C; humidity 65%) treated with a solution containing 87 mmol/100 g of reducing agent, adjusted to the applicable pH value. The quantity of waving fluid applied was calculated using the ratio 1:1.2 (1 g hair:1.2 ml waving fluid). 20 minutes was selected as the action time; the action temperature was 50° C. The hair was then fixed with a fixative containing peroxide and dried, and after being taken down from the curlers the hair was suspended in water for four hours (water bath temperature 40° C.).

The wave stability is calculated by the following formula:

$$\text{Wave stability, in \%} = \frac{l_o - l_t}{l_o - l_1} \times 100$$

where $l_o$ is the total length of the unwaved, straight strand (16.5 centimeters)

$l_t$ is the length of the strands after removal from the curlers and after being hung out for 240 minutes $l_1$ is the length of the unwaved, straight strand (35 centimeters, for an inside diameter of the curlers of 3 millimeters)

TABLE 1

| Waving ingredient | Yield in % | Elemental Analysis calculated/found |
|---|---|---|
| N-Propyl-2-mercaptoacetamide | 86 | C 45.08, H 8.32, N 10.51, S 24.07/ C 44.72, H 8.12, N 10.18, S 23.71 |
| N-(2'-Hydroxypropyl)-2-mercaptoacetamide | 64 | C 40.25, H 7.43, N 9.39, S 21.49/ C 40.25, H 7.30, N 9.16, S 21.63 |
| N-(3'Hydroxypropyl)-2-mercaptoacetamide | 42 | C 40.25, H 7.43, N 9.39, S 21.49/ C 40.21, H 6.99, N 9.05, S 21.32 |
| Thiolactic acid (2-mercaptopropionic acid) for comparison | | |

| Waving ingredient | HPLC (area %) | BP | WSN pH = 7 in % | WSN pH = 8 in % | WSN pH = 9 in % |
|---|---|---|---|---|---|
| N-Propyl-2-mercaptoacetamide | 98.069 | 76° C. 0.01 Torr | 85 | 96 | 100 |
| N-(2'-Hydroxypropyl)-2-mercaptoacetamide | 98.88 | 108° C. 0.01 Torr | 92 | 97 | 97 |
| N-(3'Hydroxypropyl)-2-mercaptoacetamide | 93.19 | 115° C. 0.01 Torr | 84 | 89 | 99 |
| Thiolactic acid (2-mercaptopropionic acid) for comparison | | | 38 | 54 | 62 |

As the standard, strands were treated with a glycerine monothioglycolate solution adjusted to pH 9. The standardized waving stabilities (WSN) given above in Table 1 pertain to this standard solution (pH=9), whose wave stability was taken as 100%.

Table 1 shows that at pH 7, 8, and 9, the waving effectiveness of the mercaptoacetamides of the invention are higher than with thiolactic acid.

Examples of Permanent Waving Compositions

Example 5

Permanent Waving Composition for Dyed Hair

| | |
|---|---|
| 10.8 g | N-Propyl-2-mercaptoacetamide |
| 0.4 g | Ammonia (25% aqueous solution) for pH adjustment |
| 2.0 g | Ammonium hydrogen carbonate |
| 5.0 g | Isopropanol |
| 2.5 g | 1,2-Propylene glycol |
| 2.5 g | 1,2-Pentanediol |
| 1.0 g | Isooctylphenol, ethoxylated with 10 Mol ethylene oxide |
| 1.0 g | Poly(dimethyldiallyammonium chloride) |
| 0.3 g | Perfume oil |
| 0.1 g | Vinylpyrrolidone/styrene mixed polymer (Antara$^R$ 430, GAF Corp., New York) |
| 74.4 g | Water |
| 100.0 g | |

The pH of this composition is 7.3.

Hair previously damaged by coloring treatments is washed with a shampoo, towel-dried, and set on curlers with a diameter of 8 millimeters. Next, the hair waving composition described above is applied evenly to the hair wound on the curlers. The hair is then covered with a plastic hood and heated for 10 minutes under a dryer hood at a temperature of 45° C. The covering is then removed; the hair is rinsed with water and oxidatively post-treated with 100 grams of a 3% aqueous hydrogen peroxide solution. After the curlers are taken out, the hair is rinsed again with water, set for a water wave, and then dried.

The result of this treatment is a uniform, elastic and durable waving of the hair.

Example 6

Permanent Waving Composition for Normal Hair

| | |
|---|---|
| 14.5 g | N-Propyl-2-mercaptoacetamide |
| 8.9 g | Ammonia (25% aqueous solution) |
| 4.0 g | Ammonium hydrogen carbonate |
| 1.0 g | 1,3-butanediol |
| 5.0 g | 1,2-Propylene glycol |
| 2.0 g | Dipropyleneglycol monoethyl ether |
| 4.0 g | Urea |
| 2.5 g | Hydrogenated castor oil, ethoxylated with 40 Mol ethylene oxide |
| 2.5 g | Lauryl alcohol, ethoxylated with 40 Mol ethylene oxide (CTFA: Laureth-4) |
| 0.5 g | Perfume oil |
| 0.1 g | Vinylpyrrolidone/styrene mixed polymer (Antara$^R$ 430, GAF Corp., New York) |
| 55.0 g | Water |
| 100.0 g | |

The pH of this composition is 8.4.

Normal hair, not previously damaged, is washed, dried with a hand towel, and wound onto curlers with a diameter of 6 millimeters. After that the hair is moistened thoroughly and evenly with the above-described hair waving composition. After an action time of 15 minutes, the hair is rinsed thoroughly with water and then oxidatively post-treated with 80 grams of a 3% aqueous hydrogen peroxide solution. After the curlers are taken out, the hair is rinsed again with water, set for a water wave, and then dried. The thus-treated hair has a uniform, lively curliness.

Example 7

Permanent Waving Composition for Normal Hair

| | |
|---|---|
| 7.7 g | N-Propyl-2-mercaptoacetamide |
| 8.7 g | N-(2'-Hydroxypropyl)-2-mercaptoacetamide |
| 8.9 g | Ammonia (25% aqueous solution) for pH adjustment |
| 5.0 g | Ammonium hydrogen carbonate |
| 1.0 g | 1,2-propanediol |
| 2.0 g | D-Glucose |
| 2.4 g | Ammonia |
| 1.5 g | Isooctylphenol, ethoxylated with 10 Mol ethylene oxide |
| 0.5 g | Poly(dimethyldiallyammonium chloride) |
| 0.5 g | Perfume oil |
| 0.1 g | Vinylpyrrolidone/styrene mixed polymer (Antara$^R$ 430, GAF Corp., New York) |
| 61.7 g | Water |
| 100.0 g | |

The pH of this composition is 8.3.

Normal hair, not previously damaged, is washed, dried with a hand towel, and wound onto curlers with a diameter of 6 millimeters. After that the hair is moistened thoroughly and evenly with the above-described hair waving composition. After an action time of 15 to 25 minutes, the hair is rinsed thoroughly with water and then oxidatively post-treated with 80 grams of a 3% aqueous hydrogen peroxide solution. After the curlers are taken out, the hair is rinsed again with water, set for a water wave, and then dried. The thus-treated hair has a uniform, lively curliness.

Example 8

Dual-Component Permanent Waving Composition for Normal Hair

Component A

| | |
|---|---|
| 4.5 g | Ammonium hydrogen carbonate |
| 0.4 g | Ammonia (25% aqueous solution) for pH adjustment |
| 2.0 g | Diethyleneglycol monoethyl ether |
| 2.0 g | 1-Methoxypropanol |
| 1.5 g | Propylene glycol |
| 0.5 g | Oleyl alcohol polyethyleneglycol ether - 5EO (CTFA: OLETH-5) |
| 0.5 g | Quaternary ammonium salt of the terpolymer of acrylic acid/diallyldimethylammonium chloride/ acrylamide (CTFA: POLYQUATERNIUM-39) Trade name: Merguat$^R$ Plus 3330 |
| 0.5 g | Perfume oil |
| 88.1 g | Water |
| 100.0 g | |

Component B

| | |
|---|---|
| 50.0 g | N-(2'-Hydroxypropyl)-2-mercaptoacetamide, 94% strength |

For the use of the dual-component permanent waving composition, 60 g of component A is mixed with 14 g of component B to make a hair waving composition that is ready to use. The mixing produces a product with a pH of 6.5.

Normal hair, not previously damaged, is washed, dried with a hand towel, and wound onto curlers with a diameter of 6 millimeters. After that the hair is moistened thoroughly and evenly with the above-described hair waving composition. After an action time of 15 to 25 minutes, the hair is rinsed thoroughly with water and then oxidatively post-treated with 80 grams of a 3% aqueous hydrogen peroxide solution. After the curlers are taken out, the hair is rinsed again with water, set for a water wave, and then dried. The thus-treated hair has a uniform, lively curliness and offers and excellently formed, stable permanent wave.

Example 9

Permanent Waving Composition for Normal Hair

| | |
|---|---|
| 7.7 g | N-Propyl-2-mercaptoacetamide |
| 8.7 g | N-(3'-Hydroxypropyl)-2-mercaptoacetamide |
| 5.0 g | Isopropyl alcohol |
| 1.0 g | 1,2-Propanediol |
| 0.5 g | Coconut oil alcohol, ethoxylated with 10 Mol ethylene oxide |
| 0.5 g | Perfume oil |
| 0.1 g | Vinylpyrrolidone/styrene mixed polymer (Antara$^R$ 430, GAF Corp., New York) |
| 76.5 g | Water |
| 100.0 g | |

The pH of this composition is 4.5.

Normal hair, not previously damaged, is washed, dried with a hand towel, and wound onto curlers with a diameter of 6 millimeters. After that the hair is moistened thoroughly and evenly with the above-described hair waving composition. After an action time of 15 to 25 minutes, the hair is rinsed thoroughly with water and then oxidatively post-treated with 80 grams of a 3% aqueous hydrogen peroxide solution. After the curlers are taken out, the hair is rinsed again with water, set for a water wave, and then dried. The thus-treated hair is uniformly curly over the entire length of the hair, which is comparable to the curliness attained by treatment with mildly alkaline permanent waving compositions.

Example 10

Permanent Waving Composition for Dyed Hair

| | |
|---|---|
| 13.7 g | N-(3'-Hydroxypropyl)-2-mercaptoacetamide, 90% strength |
| 4.4 g | Ammonia (25% aqueous solution) for pH adjustment |
| 2.0 g | Ammonium hydrogen carbonate |
| 2.0 g | Dipropyleneglycol monoethyl ester |
| 2.5 g | 1,2-Propylene glycol |
| 1.0 g | Poly(dimethyldiallyammonium chloride) |
| 0.3 g | Perfume oil |
| 2.5 g | Phosphoric acid ester of the decyl alcohol ethoxylated with 4 Mol ethylene oxide (CTFA: DECETH-4 PHOSPHATE) |
| 71.6 g | Water |
| 100.0 g | |

The pH of this composition is 7.3.

Hair previously damaged by coloring treatments is washed with a shampoo, towel-dried, and set on curlers with a diameter of 8 millimeters. Next, the hair waving composition described above is applied evenly to the hair wound on the curlers. The hair is then covered with a plastic hood and heated for 10 minutes under a dryer hood at a temperature of 45° C. The covering is then removed; the hair is rinsed with water and oxidatively post-treated with 100 grams of a 3% aqueous hydrogen peroxide solution. After the curlers are taken out, the hair is rinsed again with water, set for a water wave, and then dried.

The result of this treatment is a uniform, elastic and durable waving of the hair.

What is claimed is:

1. A process for making an N-alkylmercaptoacetamide of formula I:

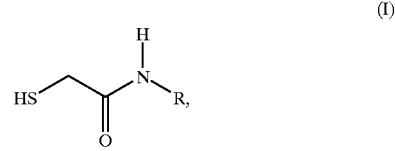

wherein R represents a straight-chain alkyl group having from 3 to 6 carbon atoms or a straight-chain hydroxyalkyl group having from 3 to 6 carbon atoms; said process comprising reacting an amine corresponding to said N-alkylmercaptoacetamide of the formula (I) with methylthioglycolate in a reaction mixture under a protective gas atmosphere at a temperature not over 30° C., extracting the reaction mixture with a solvent to form a solvent phase after the reacting and subsequently removing the solvent from the solvent phase by flash distillation to obtain said N-alkylmercaptoacetamide.

2. A composition for permanent hair waving, said composition having a pH of 4 to 8.5 and comprising water, from 3 to 28% by weight of at least one N-alkylmercaptoacetamide of formula (I) or a salt thereof, as sole keratin-reducing ingredient:

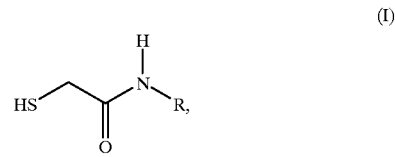

wherein R represents a straight-chain alkyl group having from 3 to 6 carbon atoms or a straight-chain hydroxyalkyl group having from 3 to 6 carbon atoms; and at least one cosmetic additive ingredient selected from the group consisting of thickeners, solubilizers, anionic surfactants, cationic surfactants, amphoteric surfactants, nonionic surfactants, alcohols, opacifiers, perfume oils, dyes, pH adjusting agents, buffer substances, sugars, stabilizers, hair-conditioning ingredients and hair-care ingredients;

wherein said surfactants, when present, are contained in a total amount of from 0.2 to 30% by weight; said alcohols, when present, are contained in a total amount of from 0.1 to 20% by weight; said opacifiers, perfume oils and said dyes, when present, are contained in respective amounts of from 0.01 to 1% by weight; said buffer substances, when present, are contained in a total amount of from 0.1 to 10% by weight; said sugars, said solubilizers, said stabilizers, said hair conditioning and said hair-care ingredients, when present, are contained in respective amounts of from 0.1 to 5% by weight and said thickeners, when present, are contained in an amount of from 0.5 to 20% by weight.

3. The composition as defined in claim 2, wherein said at least one N-alkylmercaptoacetamide is N-propyl-2-mercaptoacetamide, N-(2'-hydroxy -2-mercaptoacetamide or N-(3'-hydroxypropyl)-2-mercaptoacetamide.

4. A method for permanent waving of hair, said method comprising the steps of:

a) applying a composition for permanent waving of hair to the hair in an amount effective for the permanent waving of the hair, said composition for permanent waving having a pH of 4 to 8.5 and comprising water, from 3 to 28% by weight of at least one N-alkylmercaptoacetamide of formula (I) or a salt thereof, as sole keratin-reducing ingredient:

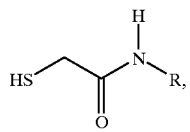

(I)

wherein R represents a straight-chain alkyl group having from 3 to 6 carbon atoms or a straight-chain hydroxyalkyl group having from 3 to 6 carbon atoms; and at least one cosmetic additive ingredient selected from the group consisting of thickeners, solubilizers, anionic surfactants, cationic surfactants, amphoteric surfactants, nonionic surfactants, alcohols, opacifiers, perfume oils, dyes, pH adjusting agents, buffer substances, sugars, stabilizers, hair-conditioning ingredients and hair-care ingredients; wherein said surfactants, when present, are contained in a total amount of from 0.2 to 30% by weight; said alcohols, when present, are contained in a total amount of from 0.1 to 20% by weight; said opacifiers, perfume oils and said dyes, when present, are contained in respective amounts of from 0.01 to 1% by weight; said buffer substances, when present, are contained in a total amount of from 0.1 to 10% by weight; said sugars, said solubilizers, said stabilizers, said hair conditioning and said hair-care ingredients, when present, are contained in respective amounts of from 0.1 to 5% by weight and said thickeners, when present, are contained in an amount of from 0.5 to 20% by weight;

b) before or after the applying of step a), setting the hair in a desired manner;

c) after the applying and the setting of steps a) and b), rinsing the hair with water;

d) after the applying and the setting of steps a) and b), oxidatively post- treating the hair;

e) after post-treating the hair oxidatively, rinsing the hair again with water and drying the hair.

5. The method as defined in claim 4, further comprising allowing said composition for permanent waving to act on the hair for from 5 to 30 minutes prior to said rinsing of the hair with water.

6. The method as defined in claim 4, further comprising allowing said composition for permanent waving to act on the hair for from 5 to 20 minutes while applying heat to the hair prior to said rinsing of the hair with water.

7. The method as defined in claim 4, wherein said amount of said at least one N-alkylmercaptoacetamide of formula (I) is from 60 to 120 grams.

8. The method as defined in claim 4, further comprising putting the hair in a wave after oxidatively post-treating the hair.

* * * * *